(12) United States Patent
Langley et al.

(10) Patent No.: US 9,375,386 B2
(45) Date of Patent: Jun. 28, 2016

(54) MULTI-DIMENSIONAL IDENTIFIER

(75) Inventors: Christopher Nigel Langley, Leamington Spa (GB); Paul Benedict Rutter, Yeomanry Close (GB); Richard James Vincent Avery, Chipping Campden (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 351 days.

(21) Appl. No.: 13/522,490

(22) PCT Filed: Jan. 21, 2011

(86) PCT No.: PCT/EP2011/050794
§ 371 (c)(1),
(2), (4) Date: Dec. 4, 2012

(87) PCT Pub. No.: WO2011/089204
PCT Pub. Date: Jul. 28, 2011

(65) Prior Publication Data
US 2013/0072894 A1    Mar. 21, 2013

Related U.S. Application Data

(60) Provisional application No. 61/297,602, filed on Jan. 22, 2010.

(30) Foreign Application Priority Data

Apr. 23, 2010   (EP) .................................... 10160862

(51) Int. Cl.
*A61J 1/18*         (2006.01)
*A61M 5/24*         (2006.01)
(Continued)

(52) U.S. Cl.
CPC ... *A61J 1/18* (2013.01); *A61M 5/24* (2013.01); *B65D 25/00* (2013.01); *G09F 3/10* (2013.01);
(Continued)

(58) Field of Classification Search
CPC .................................................. A61J 2205/30

USPC ............................ 604/404; 206/459.5, 459.1
See application file for complete search history.

(56) References Cited

U.S. PATENT DOCUMENTS 6,346,886 B1 * 2/2002 De La Huerga ........... 340/573.1
2005/0071044 A1 * 3/2005 Yonge et al. .................. 700/215
(Continued)

FOREIGN PATENT DOCUMENTS

| EP | 2282302 | 2/2011 |
| WO | 99/47062 | 9/1999 |
| WO | 01/84542 | 11/2001 |
| WO | 2008/074897 | 6/2008 |

OTHER PUBLICATIONS

International Preliminary Report on Patentability for Int. App. No. PCT/EP2011/050794, mailed Aug. 2, 2012.
(Continued)

*Primary Examiner* — Leslie Deak
*Assistant Examiner* — Kai Weng
(74) *Attorney, Agent, or Firm* — McDonnell Boehnen Hulbert & Berghoff LLP

(57) ABSTRACT

An identifier for a medicament reservoir is provided, wherein the identifier comprises a malleable sheet of material. The sheet of material comprises a top surface and a bottom surface. The bottom surface may be used to apply the identifier to a surface of the medicament reservoir. A first three-dimensional feature is attached to the sheet of material. The three-dimensional feature may be representative of a medicament contained in the reservoir and may further comprise an alignment feature. In addition, the three-dimensional feature may be coded for a particular drug delivery device. Such drug delivery devices could comprise pen type drug delivery devices.

11 Claims, 6 Drawing Sheets

(51) Int. Cl.
  *G09F 3/10* (2006.01)
  *B65D 25/00* (2006.01)
  *A61J 1/06* (2006.01)
  *G09F 1/08* (2006.01)
  *G09F 3/02* (2006.01)

(52) U.S. Cl.
  CPC ............... *A61J 1/065* (2013.01); *A61J 2205/30* (2013.01); *A61M 2205/6036* (2013.01); *A61M 2205/6045* (2013.01); *G09F 1/08* (2013.01); *G09F 2003/0264* (2013.01); *G09F 2003/0273* (2013.01); *G09F 2003/0276* (2013.01)

(56) References Cited

U.S. PATENT DOCUMENTS

2008/0164273 A1    7/2008  Dallman
2009/0294521 A1*  12/2009  de la Huerga ................. 235/375

OTHER PUBLICATIONS

International Search Report for Int. App. No. PCT/EP2011/050794, completed Jul. 15, 2011.

\* cited by examiner

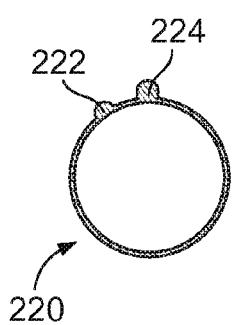 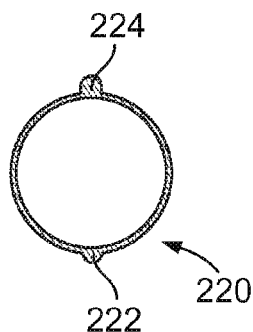 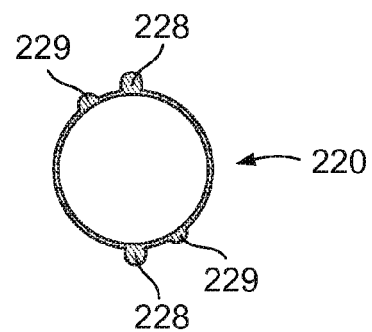
FIG. 12A          FIG. 12B          FIG. 12C
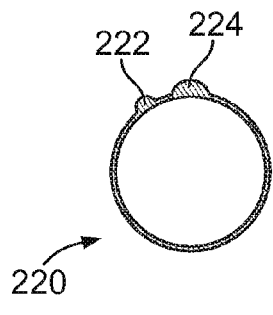 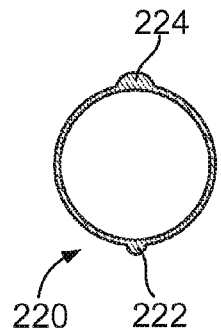 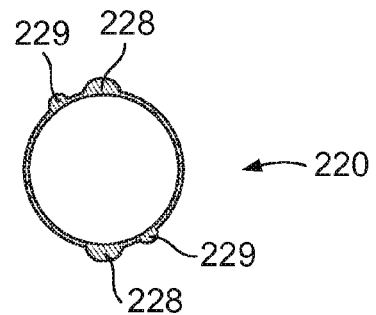
FIG. 13A          FIG. 13B          FIG. 13C

MULTI-DIMENSIONAL IDENTIFIER

CROSS REFERENCE TO RELATED APPLICATIONS

The present application is a U.S. National Phase Application pursuant to 35 U.S.C. §371 of International Application No. PCT/EP2011/050794 filed Jan. 21, 2011, which claims priority to U.S. Provisional Patent Application No. 61/297,602 filed on Jan. 22, 2010 and European Patent Application No. 10160862.8 filed on Apr. 23, 2010. The entire disclosure contents of these applications are herewith incorporated by reference into the present application.

FIELD OF INVENTION

Specific embodiments of this disclosure relate to reservoirs, particularly reservoirs containing a medicament. More particularly, the present disclosure is generally directed to reservoirs comprising a three-dimensional identifier, a label, or other similar designating element that represents or is indicative of the contents (such as a medicament) contained within the reservoir. As just one example, such medicament reservoirs may comprise an ampoule, a cartridge, a vial, or a pouch, and may be used with a medical delivery device. Exemplary medical delivery devices include, but are not limited to syringes, pen type syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient may load a cartridge containing the insulin into a cartridge housing. After the cartridge has been correctly loaded, the user may then be called upon to select a dose of medicament. Multiple doses may be dosed from the cartridge. Once the cartridge is empty, the cartridge must be removed and replaced with a new cartridge. Most suppliers of such cartridges recommend that the user may dispose of the empty cartridges properly.

Such known self administration systems requiring the removal and reloading of empty cartridges have certain limitations. For example, in certain generally known systems, a user may simply load a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, the drug delivery device does not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short-acting insulin in lieu of a long-acting insulin could result in injury or even death.

Some drug delivery devices or systems may use a color coding scheme to assist a user or care giver in selecting the correct cartridge to be used with a correct drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and must comply with certain recognized local and international standards. Consequently, such cartridges are typically supplied in standard sized cartridges (e.g., 3 ml cartridges). Therefore, there may be a variety of cartridges supplied by a number of different suppliers and containing different medicament. However, these cartridges may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps not designed or intended to be used with such a cartridge and therefore the medicament contained within that cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and to design an injection device that only accepts or works with the dedication or coded features provided on the cartridge so as to prevent unwanted cartridge cross use. Similarly, there is also a general need for a dedicated cartridge that allows the medical delivery device to be used with only an authorized cartridge containing a specific medicament and preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e. making it more difficult for counterfeiters to provide unregulated counterfeit products.

The problem to be solved by the present invention is to provide an identifier, a medicament reservoir and a drug delivery device where the safety for the user is improved.

SUMMARY

One aspect of the present disclosure relates to an identifier for a medicament reservoir. The medicament reservoir may be configured for holding a medicament, as an example, a plurality of doses of the medicament. The reservoir may comprise a cartridge, for example. The identifier may comprise at least one sheet of material. The sheet may comprise a malleable sheet of material. The sheet of material may comprise at least one three-dimensional coding feature. As an example, the sheet comprises two or more coding features. The at least one three-dimensional coding feature may be adapted and arranged to provide information related to the reservoir. In particular, the three-dimensional coding feature may be representative of the medicament contained in the medicament reservoir. In addition, the three-dimensional coding feature may be coded, in particular formed and arranged, such that it may match, in particular fit into, a drug delivery device or a reservoir retaining member of said device. In particular, the coding feature may be formed and arranged to cooperate and match with corresponding coding features provided on, along or in said device or in the reservoir retaining member of said device. In particular, insertion of a medicament reservoir comprising a coding feature which does not mate with the coding features provided on the device or the reservoir retaining member may be prevented due to mechanical cooperation of the coding feature of the medicament reservoir and the coding features of the device or the reservoir retaining member. Accordingly, the coding feature may prevent use of the medicament reservoir with an incorrect device.

According to an embodiment, the coding feature is a mechanical coding feature. In particular, the coding feature may be adapted and arranged to mechanically cooperate with corresponding coding features provided on the device or the reservoir retaining member when the medicament reservoir is inserted into the device.

The three-dimensional coding feature may be provided on or formed in the sheet of material. The sheet of material may comprise a top surface and a bottom surface. The bottom surface is preferably used to apply the identifier to a surface of the medicament reservoir. The three-dimensional coding feature may be provided on or formed on either said top surface or said bottom surface of said sheet of material. The coding feature may be a raised or a recessed feature. For example, the coding feature may comprise an embossed coding feature. Additionally or alternatively, said coding feature may comprise a resin coding feature. The embossed coding feature may be filled with a further material, e.g. a resin, in order to increase the robustness of the embossed coding feature, for example. The three-dimensional coding feature may comprise a printed coding feature, for example. In particular, the embossed coding feature may be filled with resin applied by screen printing. Alternatively, said coding feature may comprise a liquid coding feature, in particular a coding feature formed in a process using a liquid. In particular, for providing a more robust three-dimensional coding feature than the embossed coding feature, for example, the coding feature may be applied to the surface of the sheet by a printing process using a liquid or a solution containing solid particles so as to generate a raised profile. The liquid may be cured, for example. Alternatively, the coding feature may comprise a die-cast coding feature.

According to an embodiment, at least one of the coding features is releasably or permanently attached to, for example glued to, the sheet of material. In particular, the coding feature may be attached to either the top surface or the bottom surface of the sheet of material.

According to an embodiment at least one further sheet of material is provided. The further sheet of material may be provided along at least a portion of the top surface of the sheet of material. At least one of the coding features may be encapsulated between a portion of the sheet and a portion of the further sheet of material.

According to an embodiment, the further sheet of material is configured to define a profiled cut. The profiled cut may comprise at least one of the coding features. The profiled cut may be adapted and arranged to cooperate with a corresponding feature arranged, for example, at a reservoir retaining member In particular, the profiled cut may cooperate with a corresponding raised area on an inner cavity of the reservoir retaining member.

According to an embodiment, the identifier comprises at least one, preferably two or more, alignment features. The alignment feature may be configured to enable insertion of the reservoir comprising the identifier into a drug delivery device in a predefined orientation. The respective alignment feature may be configured to cooperate with a corresponding alignment feature provided at the previously mentioned reservoir retaining member, for example. In particular, the alignment feature of the reservoir retaining member must match the alignment feature of the identifier such that the reservoir retaining member may be able to receive the identifier, in particular in a given orientation which is given by the position of the respective alignment feature.

According to an embodiment, the identifier further comprises a two-dimensional coding feature. The two-dimensional feature may be provided on a surface of the identifier. The two-dimensional feature may be printed on the surface of the identifier, for example. The two-dimensional information may provide information such as the name of the medicament contained in the reservoir, for example.

A further aspect relates to a medicament reservoir. The medicament reservoir may be adapted to be used with a drug delivery device. The medicament reservoir may comprise a cartridge or vial, for example. The medicament reservoir may comprise the previously described identifier. The medicament reservoir may comprise a vessel. A medicament, as an example a plurality of doses of the medicament, may be provided in said vessel. The identifier may be configured to be, releasably or permanently, applied to said vessel. The identifier may be representative of the medicament contained in said vessel. The identifier may be coded, in particular may comprise at least one three-dimensional coding feature, such that it may be used in a drug delivery device which is adapted and arranged for using said vessel.

A further aspect relates a drug delivery device. The device may comprise a pen-type device. The drug delivery device may be configured to receive the previously described medicament reservoir. The drug delivery device may comprise a reservoir retaining member, e.g. a cartridge holder. The reservoir retaining member may be configured to hold the medicament reservoir. The reservoir retaining member may comprise an inner cavity. The inner cavity may be configured to receive and retain the medicament reservoir. The inner cavity, the reservoir retaining member and/or the device may comprise a device coding feature. The device coding feature may be adapted and arranged to cooperate with the coding feature of the medicament reservoir. Cooperation of the coding feature and the device coding feature may be configured to prevent insertion of a medicament reservoir into the reservoir retaining member when the coding feature does not mate with the device coding feature. In particular, a medicament reservoir holding the wrong medicament may be prevented from being loaded into the reservoir retaining member of the drug delivery device when the reservoir is provided with a non-mating identifier, in particular a non-mating coding feature. In this way, dispensing of a wrong medicament from the device may be prevented.

According to a preferred embodiment, an identifier for a medicament reservoir is provided, the medicament reservoir being configured for holding a medicament, the identifier comprising at least one sheet of material which comprises at least one three-dimensional coding feature, wherein the at least one three-dimensional coding feature is adapted and arranged to provide information related to the reservoir.

According to a preferred embodiment, an identifier for a medicament reservoir is provided, said identifier comprising a malleable sheet of material, said sheet of material comprising a top surface, a bottom surface, said bottom surface used to apply said identifier to a surface of said medicament reservoir and a first three dimensional feature formed in said sheet of material.

According to a preferred embodiment, an identifier for a medicament reservoir comprises a sheet of material and this sheet of material comprises a top surface and a bottom surface. The bottom surface is used to apply the identifier to a surface of the medicament reservoir. A first three-dimensional coding element is formed on either the top surface or the bottom surface of the sheet of material.

According to a preferred embodiment, a three-dimensional identifier for a medicament reservoir comprises a first sheet of material. A second sheet of material is provided along at least a portion of top surface of the first material. An encapsulated feature is provided between a portion of the first and a portion of the second sheet of material.

According to a preferred embodiment, a three-dimensional identifier for a medicament reservoir comprises a first sheet of material, a second sheet of material provided along at least a portion of a top surface of said first sheet of material, said second sheet of material defining a profiled cut, wherein said profiled cut comprises a coding feature.

According to a preferred embodiment, an identifier for a medicament reservoir, comprises a sheet of material, said sheet of material comprising a top surface, a bottom surface, said bottom surface being attachable to a surface of said medicament reservoir, and a first three dimensional coding element attached to said sheet of material.

According to a preferred embodiment, a medicament reservoir comprises a vessel and a medicament is provided in the vessel. A stopper is fixedly attached to the vessel, wherein the stopper prevents, in part, the medicament from exiting the vessel. A three-dimensional identifier is applied to the vessel. In this arrangement, the three-dimensional identifier may be representative of the medicament contained in the vessel.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIGS. 12A, 12B, and 12C illustrate cross-sectional views of various embodiments of coding and alignment features taken along line 1-1 of the arrangement shown in FIG. 11; and FIGS. 13A, 13B, and 13C illustrate cross-sectional views of various embodiments of coding and alignment features taken along 1-1 of the arrangement shown in FIG. 11.

DETAILED DESCRIPTION

Figure 1:
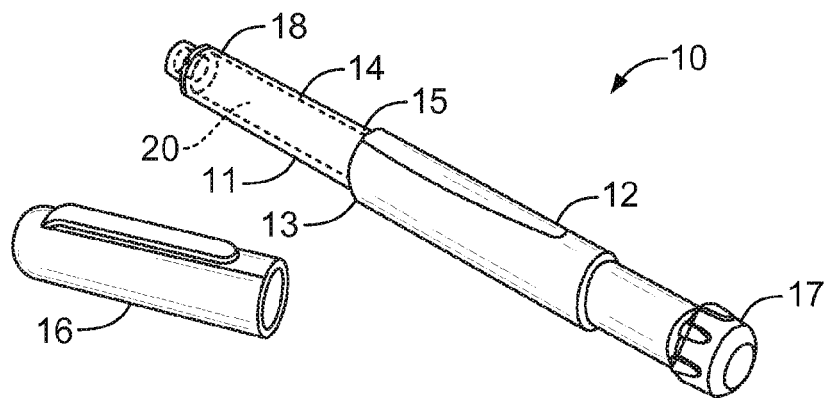
FIG. 1 illustrates a pen type drug delivery device.

Referring to FIG. 1, there is shown a drug delivery device 10 in the form of a pen type syringe. This drug delivery device or pen type syringe 10 comprises a dose setting mechanism 12, a cartridge housing 14, and a removable cap 16. A proximal end 15 of the cartridge housing 14 and a distal end 13 of the dose setting mechanism 12 may be removably secured together. When the drug delivery device 10 is not in use, the removable cap 16 can be releasably retained over the cartridge housing 14. The pen type syringe 10 may comprise a re-usable or a disposable pen type syringe. Where the syringe 10 comprises a re-usable device, the cartridge holder 14 and the dose setting mechanism 12 are preferably removably coupled together. In a disposable device 10, they may be permanently coupled together.

Figure 2:
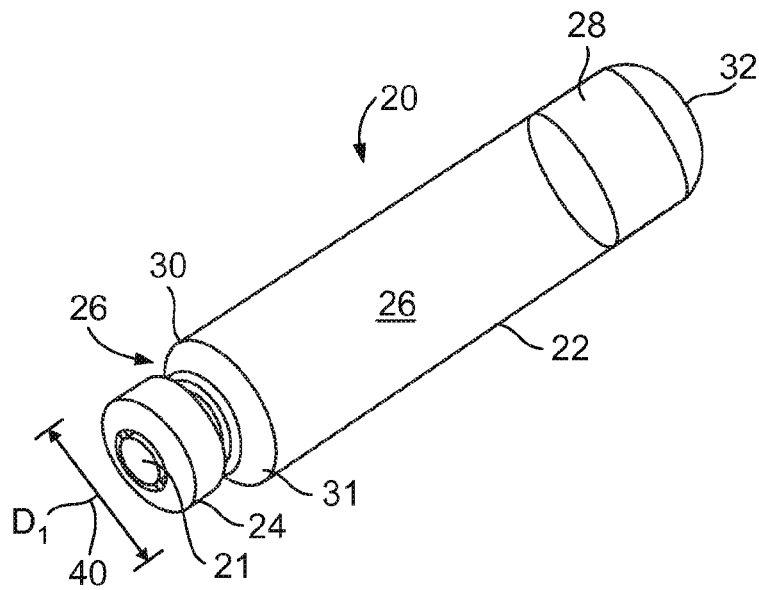
FIG. 2 illustrates a cartridge that may be loaded into a cartridge holder of the pen type drug delivery device illustrated in FIG. 1.

The cartridge housing 14 contains a removable cartridge 20 containing a medicament 26. Referring to FIG. 1, the cartridge housing 14 houses a removable cartridge 20. FIG. 2 illustrates a perspective view of the cartridge 20 that may be used with the drug delivery device 10 illustrated in FIG. 1.

An inner cartridge cavity 11 defined by the cartridge housing 14 is dimensioned and configured to securely receive and retain the cartridge 20. The cartridge 20 includes a generally tubular barrel 22 extending from a distal end 30 to a proximal end 32. The distal end 30 is defined by an inwardly converging shoulder 31.

At the distal end 30, the cartridge 20 includes a smaller diameter neck 26 and this neck projects distally from the shoulder 31 of the barrel 22. Preferably, this smaller diameter neck 26 is provided with a large diameter annular bead (not shown) and this bead extends circumferentially thereabout at the extreme distal end of the neck 26. A pierceable seal or septum 21 is securely mounted across the open distal end defined by the neck. The seal 21 may be held in place by a metallic sleeve 24. This sleeve 24 may be crimped around the circumferential bead at the distal end of the neck. The medicament 26 is pre-filled into the cartridge 20 and is retained within the cartridge 20, in part, by the pierceable seal 21, the metallic sleeve 24, and a moveable stopper 28. The stopper 28 is retained in a first end or proximal end of the cartridge 20. The stopper 28 is in sliding fluid-tight engagement with the inner tubular wall of the barrel 22. Axially directed forces in the distal direction upon the stopper 28 during dose administration urges the medication 26 from the cartridge 20 through a double ended needle (not explicitly shown) which may be mounted onto the distal end of the cartridge housing or cartridge holder 14.

A portion of the cartridge housing 14 defining the cartridge housing cavity 11 is of substantially uniform diameter represented in FIG. 2 by D1 40. This diameter D1 is preferably slightly greater than the diameter of the cartridge 20. The interior of the cartridge holder 14 includes an inwardly-extending annular portion or stop 18 that is dimensioned to prevent the cartridge 20 from moving within the cartridge holder 14. In this manner, when the cartridge 20 is loaded into the cavity 11 of the cartridge holder 14 and the cartridge holder 14 is then connected to the dose setting member 12, the cartridge 20 will be securely held within the cartridge cavity 11. More particularly, the neck 26 and crimped metallic sleeve 24 of the cartridge 20 are inserted in a proximal to distal direction into the open proximal end of the cartridge holder 14 with the crimped metallic sleeve 24 eventually passing entirely into the cartridge housing 14. With the cartridge housing 14 removably coupled to the dose setting mechanism 12, the proximal end of the cartridge 20 will typically abut a stop provided by the dose setting member 12.

A number of doses of a medicament 26 may be dispensed from the cartridge 20. Preferably, the cartridge 20 contains a type of medicament 26 that must be administered often, such as once or more times a day. One such medicament is insulin.

The dose setting mechanism 12 comprises a dose setter 17 at the proximal end of the dose setting mechanism 12. In one preferred arrangement, the dose setter 17 is rotated to set a dose. To administer this set dose, the user attaches a needle assembly comprising the previously mentioned double ended needle on the distal end of the cartridge housing 14. In this manner, the needle assembly pierces the seal 21 of the cartridge 20 and is therefore in liquid communication with the medicament 26. The user pushes on the dose setter 17 to inject the set dose. The same dose setting and dose administration procedure is followed until the medicament 26 in the cartridge 20 is expended and then a new cartridge 20 must be loaded in the device 10. To exchange an empty cartridge 20, the user is called upon to remove the cartridge housing 14 from the dose setting mechanism 12.

Figure 3:
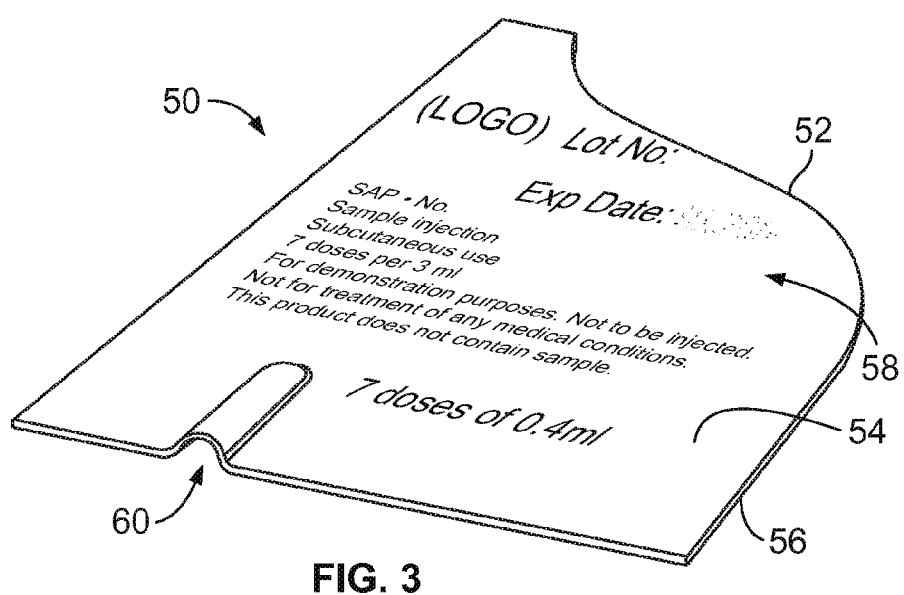
FIG. 3 illustrates a first arrangement of a three-dimensional identifier for use with a cartridge that may be used with a pen type drug delivery device, such as the drug delivery device illustrated in FIG. 1.

FIG. 3 illustrates a first arrangement of a three-dimensional identifier 50 for use with a drug delivery device, such as the device 10 illustrated in FIG. 1. In this illustration, the three-dimensional identifier 50 is shown in a generally flat state. However, as those of skill will recognize, the identifier 50 may comprise a material having a certain degree of flexibility so that the identifier 50 may be affixed to a smooth curved reservoir surface, such as the smooth curved outer surface of a conventional cartridge or vial 20 (see FIGS. 1 and 2).

In this first arrangement, the three-dimensional identifier 50 comprises a single layer of a malleable material 52 where such malleable material 52 is selected so that it is flexible about a longitudinal axis but retains its shape in the plane of the label or can be manipulated via a process to form a preferred shape or profile. Such a material 52 may comprise, for example, PE, PET, PVC, LDPE. This first material 52 has a first or top surface 54 and a second or bottom surface 56. In this arrangement, the identifier 50 comprises a flexible piece of material or film. Preferably, this material or film is provided with at least one outward facing profile 60 that can be formed in numerous ways, such as by embossing or stamping. This profile 60 may be formed by having the base material or film passed into a die with a reverse shape of a required three-dimensional profile. A stamp or punch of matching profile is used to deform the label material into a die. This stamping or punching step causes a permanent deformation in the identifier core material 52 so as to create the preferred profile 60. To increase the robustness of this embossed feature, it could be filled, for example with resin applied from a nozzle or by screen printing. As illustrated, the profile 60 created by this stamping process has a generally semi-circular shape. However, as those of ordinary skill in the art will recognize, alternative shaped profiles may also be used.

Preferably, the multi-dimensional identifier 50 also includes a two-dimensional identifier provided along the top surface 54 of the core material 52. This two-dimensional information could include information such as the name of the medicament 26 contained in the reservoir 20, information as to the supplier of the medicament 26, shelf life or expiration information of the medicament 26, recommended storage conditions, manufacturing information (lot information, date or location of manufacturing), concentration, volume, etc.

Although the identifier 50 illustrated in FIG. 3 comprises a single three-dimensional coding feature or profile 60, it will be recognized that the identifier 50 could comprise a plurality of such coding features 60. Alternatively, the identifier 50 could comprise a pattern of such profiles 60. In such an arrangement having a plurality of coding features 60, where a medicament supplier increases the number of potential three-dimensional profiles 60 and/or or profile arrangements, the number of medicaments 26 and, therefore, the number of possible coded drug containing reservoirs 20 would increase as well.

Figure 4:
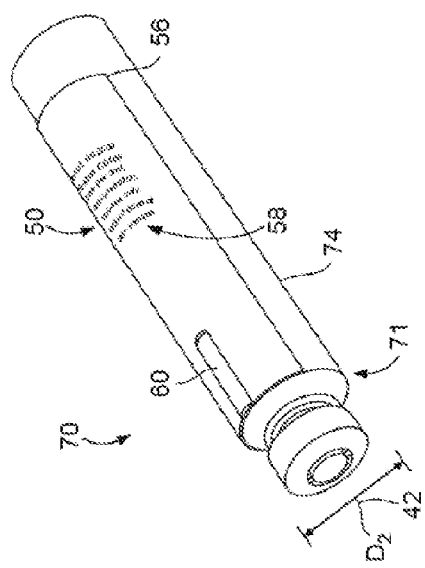
FIG. 4 illustrates the three-dimensional identifier illustrated in FIG. 3 attached to a cartridge containing a medicament.

FIG. 4 illustrates the three-dimensional identifier 50 illustrated in FIG. 3 affixed to a drug reservoir 70. Such a drug reservoir 70 could comprise a cartridge such as the cartridge 20 illustrated in FIG. 2. The identifier 50 is wrapped around and affixed to a cylindrical outer external surface of the cartridge 70.

As illustrated, the three-dimensional identifier 50 is affixed to the cartridge 70 where the bottom surface 56 of the identifier 50 is provided with a glue, an adhesive, or other similar adhering component that allows the identifier 50 to be semi-permanently affixed to an outer surface 74 of the cartridge 70. As illustrated, the identifier profile 60 is preferably located towards a distal end 71 of the cartridge 70. In this manner, when the cartridge 70 and identifier 50 are to be used with a cartridge housing, such as the cartridge housing 14 illustrated in FIG. 1, the cartridge housing 14 will need to be mechanically modified so that its inner cavity 11 is able to receive the modified dimensions of the identifier 50 so that the profile 60 can adequately pass within the inner cavity 11 of the cartridge housing 14. That is, the inner cavity 11 could now have to be modified in order to accept the cartridge 70 having a different diameter: D2 42. As just one example, the inner cavity 11 could include an indentation so as to allow passage of the protrusion 60 on the cartridge 70 as in FIG. 11. If a user were to attempt to use the cartridge or identifier system 70 illustrated in FIG. 4 with an unmodified cartridge housing 14, the profile 60 would simply prevent the cartridge 70 from being able to fit within the unmodified cartridge housing 14 and therefore inform the user that the cartridge 70 is not meant to be used with that cartridge housing 14.

In this manner, when a user attempts to load the cartridge 70 into a cartridge holder 14, the raised coding profile 60 will either allow an acceptable cartridge 70 or will prohibit an unacceptable cartridge 70 from being inserted into a drug delivery device 10. Depending on the mechanical structure of the drug delivery device 10, the cartridge 70 containing medicament 26, or the drug administration system, the coding profile 60 (or plurality of profiles or profile arrays) may be provided along a different portion of the cartridge 70 such as towards the proximal end of the cartridge 70.

The identifier 50 further comprises a two-dimensional identifier 58. In this arrangement, the identifier 50 has been applied to the cartridge 70 such that the two-dimensional identifier 58 resides near a proximal end of the cartridge 70 and the three-dimensional identifier 60 resides near a distal end of the cartridge 70. One advantage of placing this three-dimensional identifier 60 near the distal end of the cartridge 70 derives from how a user ordinarily loads a new cartridge 70 into a cartridge housing 14 of a device 10 such as a pen type drug delivery device. That is, with many typical pen type drug delivery devices 10, the user loads a new cartridge 70 into the device 10 by initially placing the distal end of the cartridge 70 into the cartridge holder 14 first. In such cases, where a user attempts to load an incorrect cartridge 70 into a cartridge holder 14, the user will be immediately alerted that they he is attempting to load an incorrect cartridge 70.

Figure 5:
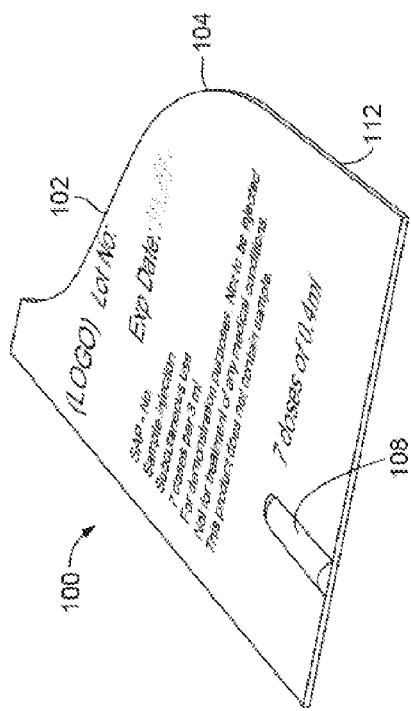
FIG. 5 illustrates a second arrangement of a three-dimensional identifier for a cartridge.

FIG. 5 illustrates an alternative three-dimensional identifier 100. This identifier comprises a first material 102 having a top surface 104 and a bottom surface 112. In an effort to provide a more robust coding feature than the stamped or embossed coding 60 feature provided by the identifier 50 illustrated in FIG. 3, the material 102 has a three-dimensional feature 108 applied to its surface by a printing process. This process may use a resin, a liquid or a solution containing solid particles so as to generate a raised profile. Examples of materials for resins are polypropylene, polyurethane, polyester, or epoxy; liquids may be an oil-based varnish; and they may contain solid particles such as glass or polymers.

As just one example, such printing could be accomplished using a computer controlled print head with nozzles dispensing a resin, a liquid or a softened plastic material. The fluid or material applied by the controlled print head can be cured or can be set using either heat, light or by reaction to air or moisture. After curing, the geometry of the raised profile or three-dimensional feature 108 becomes a fixed and integral part of the identifier 100.

Figure 6:
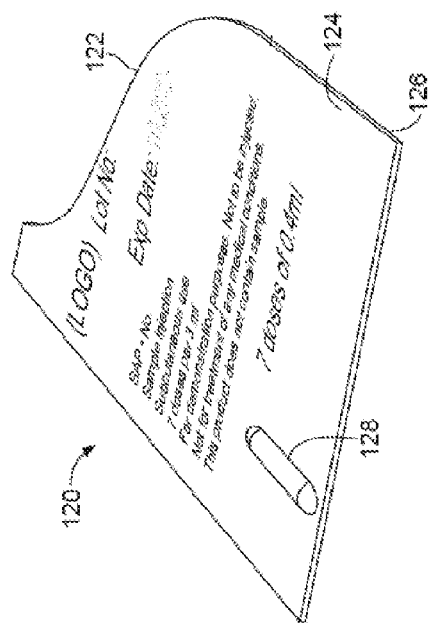
FIG. 6 illustrates a third arrangement of a three-dimensional identifier for a cartridge.

FIG. 6 illustrates yet another arrangement of a three-dimensional identifier 120. In this arrangement, the identifier 120 comprises a single layer of material or film 122. This layer of material or film 122 comprises a first or top surface 124 and a second or bottom surface 126. As with the other identifier arrangements disclosed herein, the second or bottom surface 126 may be chemically prepared for semi-permanent adhesion to a reservoir surface.

A raised coding profile 128 is cast on a first surface 124 of this single layer 122. In one preferred arrangement, this raised coding profile 128 may be cast using a viscous resin or liquid. For example, the raised coding profile 128 may have a predefined area. This predefined area may define the coding feature 128 and can be created by first coating the top surface 124 of the material 122 with a smooth gloss varnish or ink. Preferably, such varnish or ink acts as a mask so as to contain the flow of the resin or the liquid. By leaving a region of the top surface 124 of the material 122 uncoated, this will allow the cast material to bond to the top surface 124 of the identifier 120 in a pre-defined area and, hence, provide a three-dimensional coding feature 128. The casting process may transfer a resin or liquid such as polyurethane or polyester from a nozzle or dispenser onto the top surface 122 of the material 122. The applied resin or liquid may flow up to the edge of the masked area or areas and only bonds to the untreated label surface. Again, although only one profile 128 is illustrated in FIG. 6, alternative identifier arrangements utilizing a plurality of profiles or profile patterns, such as profile 128 may be utilized.

Figure 7:
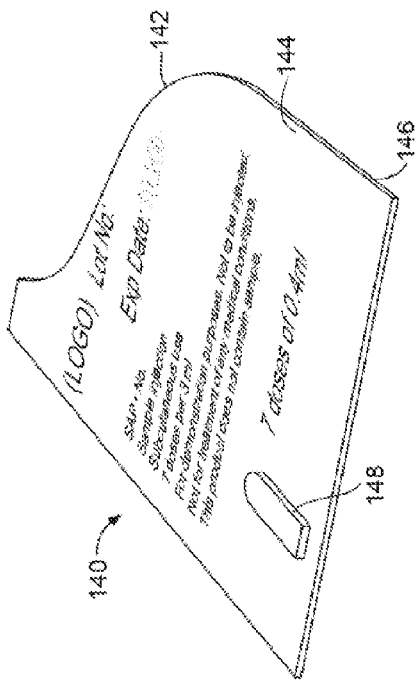
FIG. 7 illustrates a fourth arrangement of a three-dimensional identifier for a cartridge.

FIG. 7 illustrates yet another arrangement of a three-dimensional identifier 140. In this arrangement, the identifier 140 is made up of a single layer of material or a single layer of film 142. Again, this single layer of material or a single layer of film 142 comprises a top surface 144 and a bottom surface 146. A coding feature 148 could be attached to the top surface 144 of this material and this separate coding feature 148 could be attached by gluing, bonding or the application of heat. The coding feature 148 can be made as a moulded, die-cut or laser-profiled component. Once the coding feature 148 is attached to the top surface 144, the raised coding feature 148 may become an integral part of the identifier 140.

Figure 8:
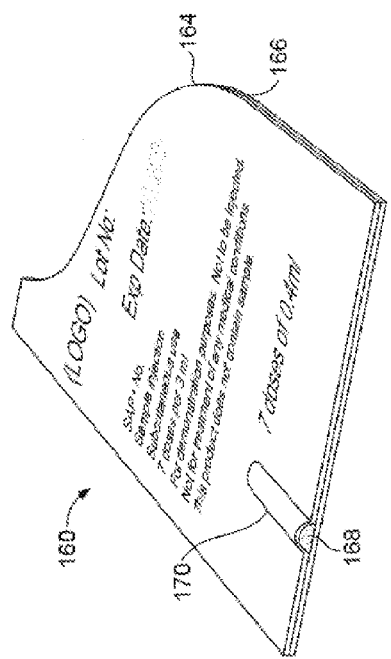
FIG. 8 illustrates a fifth arrangement of a three-dimensional identifier for a cartridge.

FIG. 8 illustrates yet another arrangement of a three-dimensional identifier 160. In this arrangement, the identifier 160 comprises two layers of material or film: a first layer 164 and a second layer 166. These two layers of material 164, 166 may be used to encapsulate a separate coding feature 168. This encapsulated coding feature 168 defines along with the first material 164 a raised coding feature 170. In one arrangement, the first layer 164 and the second layer 166 may be placed around a moulded, die-cut or laser-profiled component. In one preferred arrangement, the process of bonding the first and the second layers 164, 166 together under the application of heat causes the first layer 164 to deform around the coding feature 168. The resulting change in surface profile provides the three-dimensional coding feature 168 of the identifier 160.

In an alternative arrangement, the first layer 164 of the identifier 160 could be embossed using a die tool to create a raised profile. Once this raised profile 168 is defined, the individual profiled component could then be placed in the embossed area. The second layer 166 of the identifier 160 could then be applied to the embossed first layer 164 and individual profiled component 168 to thereby encapsulate the profiled component 168 to create the identifier 160.

In yet another alternative arrangement, a further process could use an embossed first layer 164 into which a resin is applied from a nozzle or by a screen printing process. The second layer 166 would encapsulate the resin to form the finished identifier 160. The coding detail is provided by the raised profile 168 encapsulated between the first and second layers 164, 166 of material or film.

Figure 9:
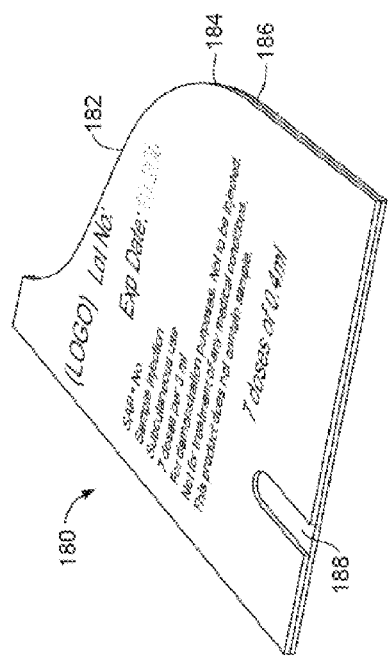
FIG. 9 illustrates a sixth arrangement of a three-dimensional identifier for a cartridge.

FIG. 9 illustrates yet another arrangement of a three-dimensional identifier 180. In this arrangement, the identifier 180 comprises a first or a top layer 184 and a second or bottom layer 186 of material or film 182. Alternatively, the identifier 180 may comprise more than two layers of material or film 182. As illustrated, the top layer 184 defines a profiled cut 188 that defines the area of material to be removed. Stripping away or removing the cut profile creates a recessed zone 188 within a first surface of the identifier 180.

This change in surface height can provide a coding feature 188 that fits within a corresponding raised area on the inner cavity 11 of the cartridge holder, such as the cartridge holder 14 illustrated in FIG. 1. Matching the two parts together on assembly of the cartridge housing 14 to the dose setting mechanism 12 will confirm that a correct cartridge has been loaded into the cartridge holder 14 and hence the drug delivery device 10.

Figure 11:
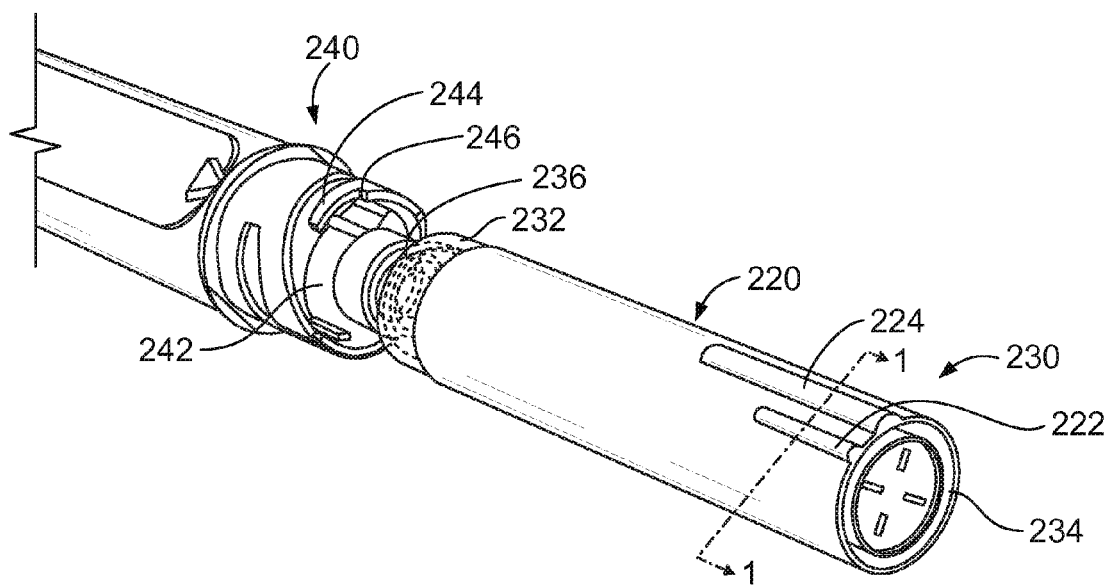
FIG. 11 illustrates a seventh arrangement of a three-dimensional identifier for a cartridge.

FIG. 11 illustrates another arrangement of a three-dimensional identifier 220. If one coding feature is unique, that coding feature can be used to align another coding feature. This is shown in FIG. 11. In FIG. 11, the three-dimensional identifier 220 is shown affixed to an outer surface 232 of a cartridge 230. The identifier 220 comprises two raised features: a male coding feature 222 and a male alignment feature 224, shown at the proximal end 234 of cartridge 230. An inner cavity 242 of a cartridge housing 240 comprises a corresponding female coding feature 244 and female alignment feature 246. The male coding feature 222 and male alignment feature 224 on cartridge 230 must match the female coding feature 244 and female alignment feature 246 so that the inner cavity 242 is able to receive the identifier 220, allowing the male features to adequately pass within the inner cavity 242 of the cartridge housing 240. Although the male coding feature 222 and the male alignment feature 224 are shown at the proximal end 234 of cartridge 230, male coding feature 222 and male alignment feature 224 may be located at any position along cartridge 230. The features may be located at or near the distal end 236 of cartridge 230, or at an intermediate position along cartridge 230.

FIGS. 12A, 12B, and 12C illustrate cross-sectional views of various embodiments of coding and alignment features, taken along line 1-1 of the arrangement shown in FIG. 11. FIGS. 12A and 12B show various arrangements of male alignment feature 224 and male coding feature 222. In FIGS. 12A and 12B, male alignment feature 224 may comprise a thicker protrusion than male coding feature 222, so that the alignment features 224 cannot fit into the indentation arranged in the inner cavity 242 of the cartridge housing 240 and intended for cooperation with the coding features 222. As demonstrated in FIGS. 12A and 12B, male alignment feature 224 and male coding feature 222 may be present at various locations along the circumference of identifier 220. FIG. 12C illustrates an alternative identifier 220, comprising two identical sets of male alignment features 228 and male coding features 229, arranged axisymmetrically so that the cartridge 230 can be inserted in either of two orientations. Other numbers of male alignment features and male coding features may be present on three-dimensional identifier 220.

FIGS. 13A, 13B, and 13C illustrate cross-sectional views of various embodiments of coding and alignment features, taken along line 1-1 of the arrangement shown in FIG. 11. FIGS. 13A and 13B show male alignment feature 224 as having a larger width than male coding feature 222. As demonstrated in FIGS. 13A and 13B, male alignment feature 224 and male coding feature 222 may be present in various locations along the circumference of identifier 220. FIG. 13C illustrates an alternative identifier 220, comprising two identical sets of male alignment features 228 and male coding features 229, arranged axisymmetrically so that the cartridge 230 can be inserted in either of two orientations. Other numbers of male alignment features and male coding features may be present on three-dimensional identifier 220.

The arrangements of FIGS. 11 and 12A allow for clearance between the cylindrical surfaces of the cartridge 230 and the cartridge housing 240, preventing sticking of the cartridge 230 to the cartridge housing 240 due to ovality or other tolerances. As illustrated with both the alignment feature 224 and coding feature 222 on the same side of the cartridge 230, the cartridge 230 may be pushed off-center allowing an incorrect cartridge 230 to be fitted. This problem can be reduced if coding and/or alignment features are arranged axisymmetrically, as illustrated in 12B and 12C.

In addition, arrows may be present on both the male alignment feature and the female alignment feature so that a user can easily identify which features should be aligned.

The three-dimensional coding system results in a number of advantages. For example, the coding system may assist the user to distinguish between medicaments, thereby helping to ensure that a delivery device can only be used with a medicament for which the device is intended. In particular, with the proposed three-dimensional coding system applied to a cartridge, the cartridge may be prevented from being loaded into a drug delivery device when the cartridge comprises an incorrect identifier. The cartridge identifier prevents a user from completing one or more of the following actions: fully inserting the cartridge into an incorrect cartridge holder or attaching the cartridge and/or cartridge holder onto an incorrect dose setting mechanism.

Although aimed primarily at the insulin market, the presently disclosed multi-dimensional identifier may apply to other medicaments as well. For example, as illustrated in FIG. 1, one preferred application of the presently disclosed multi-dimensional identifier can be applied to various drug delivery devices, including the following examples; an injector pen with a cartridge (e.g., 3 ml cylindrical cartridge) and a separate cartridge housing as illustrated in FIG. 1. Furthermore, the identifier may be applied to an injector pen with a cartridge (e.g., 3 ml cylindrical glass cartridge) non removably retained in a holder, so that the holder will be disposed of with the primary pack and to an injector pen where the primary pack attaches directly to the pen, e.g. an injection moulded polymer cartridge.

Figure 10:
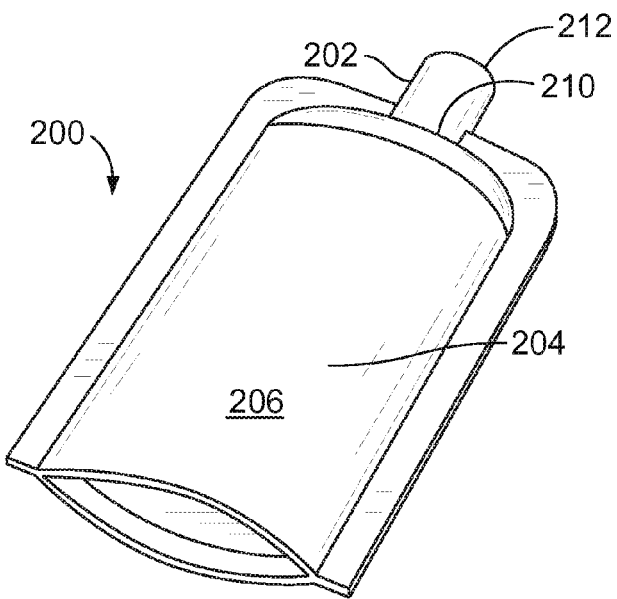
FIG. 10 illustrates an alternative reservoir that may be used with the three-dimensional identifier.

Furthermore, the identifier may apply to any drug delivery device, with any type of reservoir or primary pack, e.g. a inhaler or a pouch. For example, FIG. 10 illustrates a drug reservoir 200 comprising a vessel 204 that contains a medicament 206. A stopper 210 is provided along a distal end of the vessel 204 and is attached to the vessel 204 so as to prevent the medicament 206 from exiting the vessel 204. In yet another arrangement, a three-dimensional identifier 202 is provided on the vessel 204 near an output port 212 of the vessel 204. This output port 212 has a rigid neck and a three-dimensional identifier 202 is provided along this neck.

The identifier may also apply to various components within a device, including the following examples, and to any location on the components, e.g. at the distal or proximal end, or in an intermediate position:

the interface between a cartridge (or a feature attached to the cartridge) and its holder;

the interface between a cartridge (or a feature attached to the cartridge) and the drug delivery device; and the interface between a cartridge holder, moulded cartridge, or other primary pack and the drug delivery device.

The three-dimensional identifier may result in a number of advantages. For example, the three-dimensional identifier may result in a low cost coding mechanism since it is formed on a label which is already applied to the cartridge and can be manufactured in a cost effective manner. Moreover, there are quite a large number of different coding configurations that may be used. Consequently, with proposed three-dimensional coding schemes, a large number of medicaments can be distinguished from one another. In addition, with the three-dimensional coding scheme, if a user attempts to load an incorrect reservoir into a cartridge holder designed for a different cartridge, the user will be alerted at an early stage of the assembly process.

Exemplary embodiments of the present invention have been described. Those skilled in the art will understand, however, that changes and modifications may be made to these arrangements without departing from the true scope and spirit of the present invention, which is defined by the claims.

The invention claimed is:

1. An identifier for a medicament reservoir, the medicament reservoir with a proximal end and a distal end having a pierceable septum on said distal end being configured for holding a medicament, the identifier comprising at least one sheet of material which comprises at least one three-dimensional coding feature, wherein the at least one three-dimensional coding feature is adapted and arranged to provide information related to the reservoir, and wherein at least one of the three-dimensional coding features is encapsulated between the sheet of material and at least one further sheet of material, further comprising at least one alignment feature separate from the at least one three-dimensional coding feature which is configured to enable insertion of the reservoir comprising the identifier into a drug delivery device in a predefined orientation, wherein the alignment feature comprises a thicker protrusion than the coding feature, wherein the alignment feature and coding feature are on the proximal end of the reservoir opposite the pierceable septum.

2. The identifier of claim 1, wherein the at least one sheet of material comprises a top surface and a bottom surface, the bottom surface being configured to apply the identifier to a surface of the medicament reservoir.

3. The identifier according to claim 1, where the at least one further sheet of material is provided along at least a portion of the top surface of the sheet of material.

4. The identifier according to claim 3, wherein the further sheet of material is configured to define a profiled cut, wherein the profiled cut comprises at least one of the three-dimensional coding features.

5. The identifier according to claim 1, wherein at least one of the three-dimensional coding features comprises an embossed coding feature.

6. The identifier according to claim 1, further comprising a printed coding feature or a raised coding feature formed by casting.

7. The identifier according to claim 1, wherein at least one of the three-dimensional coding features comprises a resin coding feature or a liquid coding feature.

8. A medicament reservoir used with a drug delivery device, the medicament reservoir comprising the identifier according to claim 1 and a vessel wherein a medicament is provided in said vessel.

9. A drug delivery device configured to receive the medicament reservoir according to claim 8 and comprising a reservoir retaining member configured to hold the medicament reservoir.

10. The drug delivery device according to claim 9, wherein the reservoir retaining member comprises a device coding feature which is adapted and arranged to cooperate with the three-dimensional coding feature of the medicament reservoir.

11. The drug delivery device according to claim 10, wherein cooperation of the three-dimensional coding feature and the device coding feature is configured to prevent insertion of a medicament reservoir into the reservoir retaining member when the coding feature does not mate with the device coding feature.

* * * * *